(12) United States Patent
Gaiser et al.

(10) Patent No.: US 8,706,995 B2
(45) Date of Patent: Apr. 22, 2014

(54) FIELD DEVICE WITH SEPARATED MEMORY AREAS

(75) Inventors: Martin Gaiser, Aplirsbach (DE); Juergen Haas, Oberwolfach (DE); Juergen Lienhard, Fischerbach (DE); Juergen Motzer, Gengenbach (DE)

(73) Assignee: VEGA Grieshaber KG, Wolfach (DE)

( * ) Notice: Subject to any disclaimer, the term of this patent is extended or adjusted under 35 U.S.C. 154(b) by 903 days.

(21) Appl. No.: 12/603,050

(22) Filed: Oct. 21, 2009

(65) Prior Publication Data

US 2010/0125427 A1    May 20, 2010

Related U.S. Application Data

(60) Provisional application No. 61/115,225, filed on Nov. 17, 2008.

(30) Foreign Application Priority Data

Nov. 17, 2008 (EP) ..................................... 08169291

(51) Int. Cl.
*G06F 12/00* (2006.01)

(52) U.S. Cl.
USPC ......................................... 711/163; 73/290 R

(58) Field of Classification Search
None
See application file for complete search history.

(56) References Cited

U.S. PATENT DOCUMENTS

| | | | |
|---|---|---|---|
| 6,148,384 A | 11/2000 | Devanagundy et al. | |
| 7,018,800 B2 | 3/2006 | Huisenga et al. | |
| 7,280,048 B2 | 10/2007 | Longsdorf et al. | |
| 8,037,753 B2 | 10/2011 | Fehrenbach et al. | |
| 2004/0227635 A1 | 11/2004 | Sabatino | |
| 2004/0243351 A1* | 12/2004 | Calkins et al. | 702/185 |
| 2005/0075844 A1* | 4/2005 | Mueller et al. | 702/189 |
| 2008/0140957 A1* | 6/2008 | Pattabiraman et al. | 711/161 |
| 2008/0162867 A1* | 7/2008 | Shin et al. | 711/173 |
| 2009/0071245 A1* | 3/2009 | Harazin et al. | 73/290 R |

FOREIGN PATENT DOCUMENTS

| | | |
|---|---|---|
| CN | 1688869 | 10/2005 |
| WO | 00/03209 | 1/2000 |
| WO | 2004/104525 | 12/2004 |
| WO | 2006/104712 | 10/2006 |

OTHER PUBLICATIONS

Pattabiraman et al., "Software Critical Memory: All Memory is not Created Equal:", Microsoft Research, MSR-TR-2006-128, Sep. 2006, pp. 1-12, XP 002525828, Remond, WA, USA.

Saltzer et al., "The Protection of Information in Computer Systems", Proceedings of the IEEE USS, vol. 63, No. 9, Sep. 1975, XP 002525829, pp. 1278-1308.

\* cited by examiner

*Primary Examiner* — Matthew Bradley
*Assistant Examiner* — Daniel Tsui
(74) *Attorney, Agent, or Firm* — Fay Kaplun & Marcin, LLP

(57) ABSTRACT

A field device for measuring a filling level, a pressure or a density of a medium in a container includes data memory with two memory areas that are separated from one another. First data for safety-critical program modules is stored in the first memory area. Second data for safety-uncritical program modules is stored in the second memory area. The two memory areas are separated from one another. All access to these memory areas is controlled by a memory management unit.

12 Claims, 2 Drawing Sheets

FIELD DEVICE WITH SEPARATED MEMORY AREAS

REFERENCE TO RELATED APPLICATION

This application claims the benefit of the filing date of EP Patent Application Serial No. 08 169 291.5 filed on Nov. 17, 2008 and U.S. Provisional Patent Application Ser. No. 61/115,225 filed on Nov. 17, 2008, the disclosure of which applications is hereby incorporated herein by reference.

FIELD OF THE INVENTION

The invention pertains to filling level, pressure and density measurements. The invention specifically pertains to a field device for measuring a filling level, a pressure or a density of a medium, a method for measuring and determining a level, a pressure or a density of a medium, a program element, as well as a machine-readable medium.

TECHNOLOGICAL BACKGROUND

Developments for the sector "functional safety" in the field of level, pressure or density measurements require a high expenditure of time and qualification of the development team.

The devices that perform a safety function usually have other functions that do not contribute to performing the safety function. Safety-irrelevant functions need to be examined with respect to their repercussions on the safety function.

This may result in these functionalities also being categorized as critical such that the development expenditures are increased accordingly.

SUMMARY OF THE INVENTION

Disclosed are a field device for measuring a filling level, a pressure or a density of a medium in a container, a method for measuring and determining a filling level, a pressure or a density of a medium in a container, a program element and a machine-readable medium The described embodiments likewise pertain to the field device, the method, the program element and the machine-readable medium. In other words, characteristics that are described below with reference to the field device can also be implemented in the method, the program element or the machine-readable medium and vise versa.

According to one embodiment of the invention, a field device for measuring a filling level, a pressure or a density of a medium in a container is provided, wherein said field device contains a data memory. The data memory is divided into at least one first and one second memory area that are separated from one another. The first memory area stores the data of program modules that are required for the safe operation of the field device and therefore categorized as a safety-critical ("first data"). The second memory area only stores the data of program modules that are not required for the safe operation of the field device and therefore categorized as safety-uncritical ("second data").

This may make it possible to separate safety-critical functions of the field device and safety-uncritical functions of the field device (such as, for example, diagnosis, data logger, statistics, measured value indicator).

In particular, this may provide for a field device that fulfills stricter safety requirements.

Due to the separation of the functions, the safety-uncritical or safety-irrelevant functions may be developed with lower expenditures. Consequently, it may also be possible to utilize software components that already exist or are purchased and do not fulfill any strict requirements with respect to the safety integrity.

The safety requirement level to be fulfilled by a particular program module determines whether the program module is categorized as safety-critical or safety-uncritical. The safety requirement level is a term from the field of functional safety and also referred to as safety integration level (SIL). The desired safety requirement level defines the safety-oriented construction principle that needs to be observed so that the risk of a malfunction fulfills the specified requirements.

If a program module is categorized as safety-critical, this means, for example, that this program module needs to fulfill the requirements of SIL3 or even SIL4. If a function is categorized as safety-uncritical, this means, for example, that it has to fulfill the requirements of SIL 0.

According to another embodiment of the invention, a memory management unit is provided that manages and, if applicable, also controls access to the different data.

The memory management unit preferably consists, for example, of a so-called Memory Management Unit (MMU). The memory management unit serves, for example, for isolating processes (i.e., the different program modules) from one another and from the operating system. The memory management unit may consist of an external auxiliary component of a microprocessor. It may also be integrated into the microprocessor. The memory management unit also controls, in particular, memory protection tasks. For example, individual memory areas may be blocked with respect to the execution by certain program modules or blocked with respect to writing additional data therein.

According to another embodiment of the invention, the separation of the two memory areas is realized in such a way that none of the data stored in the first memory area can be unintentionally altered because the program modules that are categorized as safety-uncritical do not have access to this data.

According to another embodiment of the invention, a real-time operating system is provided that corresponds to the safety requirements of the field device and supports the memory management unit.

According to another embodiment of the invention, the operating system is designed for establishing or realizing communications between the individual program modules.

The operating system is able, in particular, to manage and to monitor the data exchange between the two separated memory areas.

According to another embodiment of the invention, the first memory area contains a data memory of a program module provided for performing a function that concerns the determination of measured values on the basis of sensor measuring data, the derivation of additional measured values on the basis of already determined measured values, the output of measured values and/or the diagnosis.

In the context of the invention, this concerns safety-relevant functions.

According to another embodiment of the invention, the second memory area contains a data memory of a program module that is designed for establishing a connection with an external communication unit, for recording measured values with status information as a function of the time, for indicating measured values and/or for adjusting values in the field device.

In the context of the invention, this concerns safety-irrelevant functions.

According to another embodiment of the invention, the field device is designed for the cyclic processing of the determination of measured values, the derivation of measured values and the output of measured values.

According to another embodiment of the invention, the field device is designed for carrying out the diagnosis parallel to the acquisition of measured values and features a measured value recorder that checks after each determination of a measured value if the corresponding measured value needs to be recorded. For example, this measured value can then be stored redundantly, i.e., in the first memory area as well as in the second memory area.

According to another embodiment of the invention, the field device comprises of a level measuring device that utilizes radar signals, controlled microwave signals, ultrasonic signals or capacitive signals. The field device may also be realized in the form of a limit level measuring device.

According to another embodiment of the invention, a method for measuring and determining a filling level, a pressure or a density of a medium in a container by means of a field device is disclosed, wherein program modules are executed that are required for the safe operation of the field device and therefore categorized as a safety-critical, and wherein the data of the program modules is stored in a first memory area of a data memory. In addition, program modules are executed that are not required for the safe operation of the field device and therefore categorized as safety-uncritical, wherein the data of these program modules is stored in a second memory area of the data memory. The two memory areas are separated from one another.

According to another embodiment of the invention, the method features the additional step of establishing communications between the two memory areas with an operating system that corresponds to the safety requirements of the field device.

According to another embodiment of the invention, a program element for measuring and determining a level, a pressure or a density of a medium in a container by means of a field device is disclosed, wherein said program element instructs a processor to carry out the above-described process steps when it is executed on the processor.

According to another embodiment of the invention, a machine-readable medium is disclosed, on which a program element for measuring and determining a level, a pressure or a density of a medium in a container by means of a field device is stored, wherein said program element instructs a processor to carry out the above-described process steps when it is executed on the processor.

In this case, the program element may consist, e.g., of part of a software that is stored on a processor of the field device. The processor may also form an object of the invention in this case. This embodiment of the invention furthermore comprises a program element that already utilizes the invention from the beginning, as well as a program element that prompts an existing program to utilize the invention by means of an update (update).

Embodiments of the invention are described below with reference to the figures.

DETAILED DESCRIPTION OF EMBODIMENTS

The figures show schematic illustrations that are not true-to-scale.

In the following description of the figures, identical or similar elements are identified by the same reference symbols.

Figure 1:
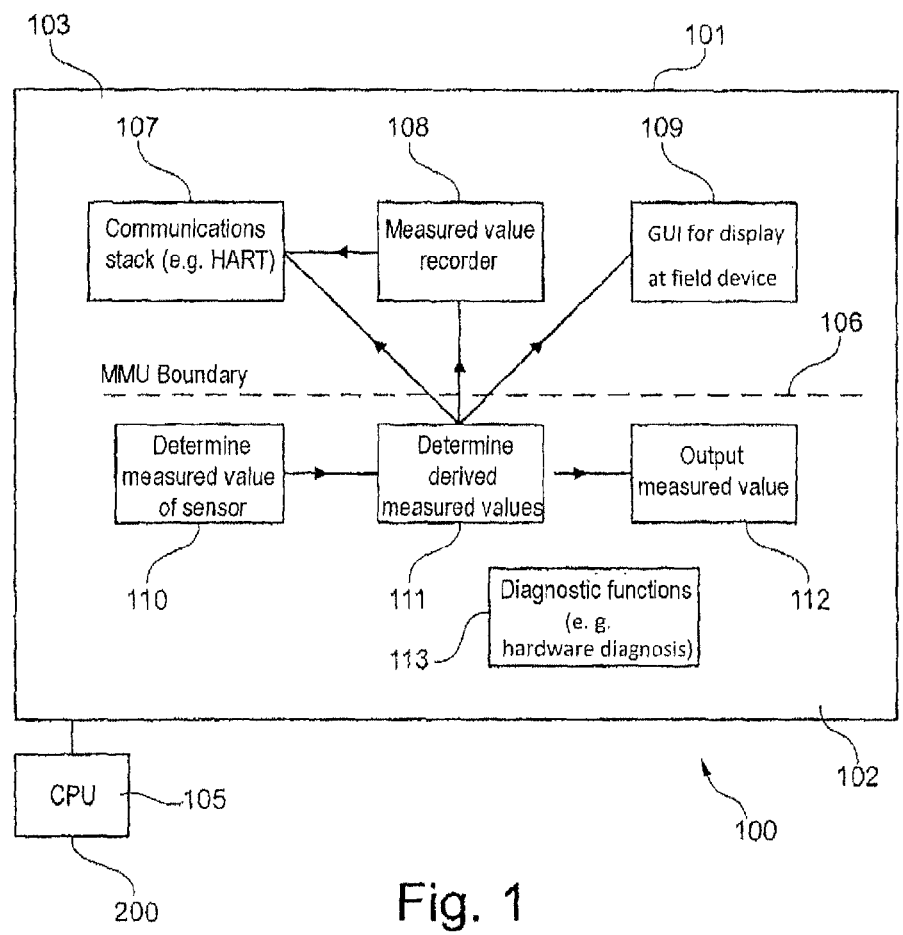
FIG. 1 shows an illustration of the electronics for a field device according to one embodiment of the invention.

FIG. 1 shows an electronic module 100 for a field device that features a data memory 101, as well as a processor, for example, in the form of a CPU 105.

The data memory 101 is divided into two areas 102, 103 that are separated from one another. The broken line 106 symbolizes the so-called MMU boundary between these two areas 102, 103.

The data (first data) of the (safety-critical) first software modules with the safety-critical functions is stored and executed in the first memory area 102. The memory protection (MMU) separates the first memory area from the (second) data of the (safety-uncritical) second software modules that do not contribute to performing the safety function and therefore are stored and executed in the second memory area 103.

During the safety function, it may therefore be impossible to unintentionally alter any value in the memory that is used by the safety function of the field device. This means that independence with respect to the data is realized.

An independence in the execution time between the safety function and other functions in the field device may be achieved, e.g., with a chronological and logical program sequence control.

The data of the safety-relevant functions or program modules that is stored in the first memory area 102 consists, for example, of the determined measured values of the sensor, the determined derived measured values, the measured values to be output and data with respect to diagnostic functions.

In order to determine the measured values, the physical quantity to be measured is ascertained with the aid of a sensor element (e.g., a pressure cell). The measured value is then read into an evaluation device by the sensor in the form of a current value or digitally with the aid of a protocol.

In order to determine the derived measured values, additional measured values are ascertained based on determined measured values. This concerns, e.g., the filling height of the medium in the container, corresponding height-percentage values, corresponding volume-proportional values or current values to be output.

The output of measured values can be realized with a correspondingly adjusted output current for a 4 . . . 20 mA interface or in the form of a digital output value with the aid of a protocol that fulfills the requirements of the safety function.

The diagnostic functions monitor the execution of the measuring functions and can test the hardware used for malfunctions.

The measured values are determined in a program module that may access the data in the memory area 110. The determined measured values are subsequently used by another program module that determines measured values derived therefrom and stores these measured values in the memory area 111. The measured values to be output are stored in the memory area 112. All these memory areas are arranged in the first memory area 102.

The reference symbol 113 symbolizes a memory area for the diagnostic functions (e.g., hardware diagnosis) in the first memory area 102 for program modules.

The data memory areas 107, 108, 109 are arranged in the separate second memory area 103. This concerns data for safety-relevant functions such as, for example, the so-called communications stack. This function establishes the connection with external communication units. This makes it possible, e.g., to transmit measured values or diagnostic values or to alter adjustments in the device.

It is also possible to provide data 108 for a measured value recorder. This recorder records the measured values with status information as a function of the time. This information can be used, e.g., for the diagnosis of the measuring task.

The data 108 of the measured value recorder can be fed to the communications stack 107.

In addition, it is possible to provide data 109 for a program module for initializing a graphical user interface (GUI) in order to realize an in-situ indication for a user. This program module can be used for indicating measured values and for adjusting values in the field device.

The three memory areas 107, 108 and 109 receive data (for example, in the form of measured values and/or derived measured values) from the first memory area 102. The communication between the two memory areas and between the program modules stored in the two memory areas is exclusively realized with an operating system that is specially provided for this purpose. In other respects, the two memory areas are completely separated from one another.

For example, the real-time operating system 105 runs on a processor 200 that is connected to the data memory 101 or on which the data memory 101 is arranged.

During the measurement, the field device processes the program modules "determine measured value," "determine derived measured values" and "output measured value" in a cyclic fashion. The diagnosis is carried out parallel to this measuring function. The measured value recorder checks after each measuring cycle if the value should be recorded. Inquiries via the communications stack reach the measuring task in an asynchronous fashion and need to be answered within a certain period of time.

The measured value chain may, in principle, be present in the device in multiple form. The measured values may be stored, in particular, in the first memory area, as well as in the second memory area.

Figure 2:
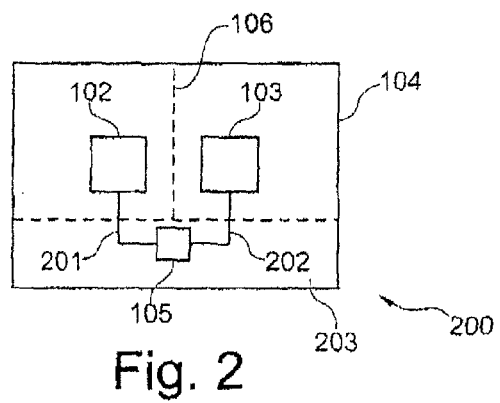
FIG. 2 shows an illustration of the electronics for a field device according to another embodiment of the invention.

FIG. 2 shows a processor 200 or a memory for a field device that features a memory area 104. This memory area is divided into at least two areas 102, 103 that are mutually access-protected by means of a MMU.

The reference symbol 106 symbolizes the separation between the two memory areas 102, 103.

It is also possible to provide a third memory area 203 that can only be used by the real-time operating system 105. The real-time operating system 105 corresponds to the SIL of the field device and supports the use of the MMU. This operating system provides communication options between the different separated memory areas 102,103. In other words, the operating system 105 makes it possible to exchange data between the two memory areas 102, 103 via the communication paths 201, 202.

The software modules of the safety function are used in such a way that they can only access the data in the protected memory area 102. The software modules of the other functions are used in such a way that they can only access the other data in the memory area 103.

One example for a program module that is categorized as safety-critical and therefore accesses the first memory area 102 is, for example, the protection from overfilling during the determination of a level. Safety-uncritical functions are, e.g., data logger, statistics or measured value indicator.

Figure 3:
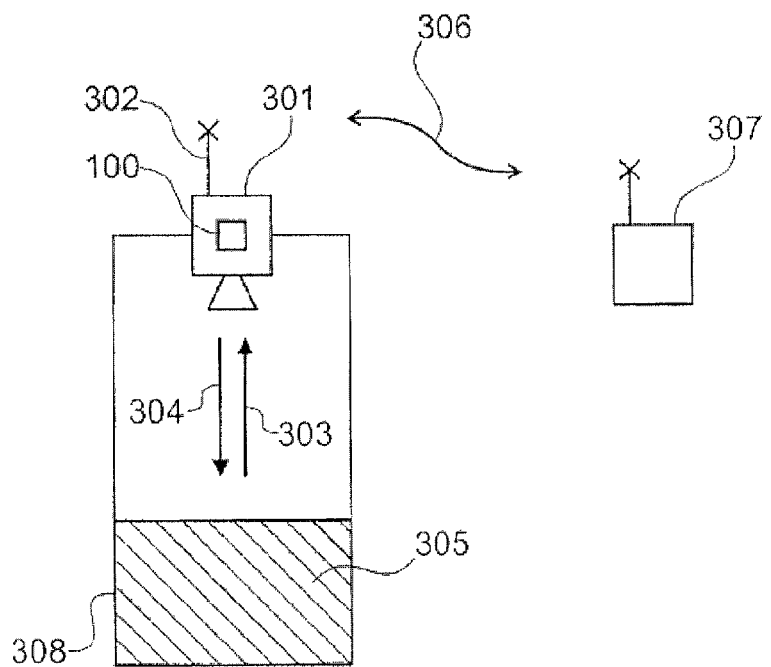
FIG. 3 shows a level measuring device according to one embodiment of the invention.

FIG. 3 shows a level measuring device 301 that is installed into a tank 308 and features an electronic module 100. The level measuring device 301 transmits a measuring signal 304 in the direction of the surface of the bulk material 305. This measuring signal is reflected on the surface of the bulk material and the corresponding reception signal 303 is subsequently received by the level measuring device 301 and evaluated. A data exchange with an external evaluation unit 307 can be realized with the antenna 302 and the communication link 306.

Figure 4:
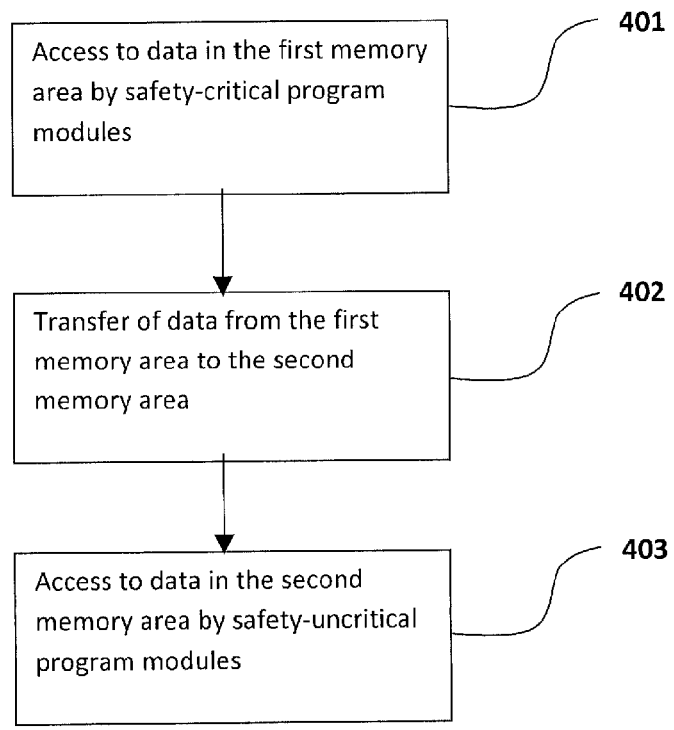
FIG. 4 shows a flow chart of a method according to one embodiment of the invention.

FIG. 4 shows a flow chart of a method according to one embodiment of the invention. Safety-critical program modules that access data in a first memory area of a data memory are executed in step 401. In step 402, certain data is transferred from the first memory area into a second memory area that is categorized as less safety-critical. This data transfer is controlled exclusively by the real-time operating system of the field device. Program modules that are categorized as safety-uncritical and access data in the second memory area are executed in step 403.

It should be pointed out that, for the purpose of the invention, safety-critical program modules (i.e., certain program modules) could also be stored in an above-described first memory area. Safety-uncritical program modules (program modules) could be just as well stored in an above-described second memory area.

As a supplement, it should be noted that "comprising" and "featuring" do not exclude other elements or steps, and that "an" or "a" does not exclude a plurality. It should furthermore be noted that characteristics or steps that were described with reference to one of the above embodiments can also be used in combination with other characteristics or steps of other above-described embodiments. The reference symbols in the claims should not be interpreted in a restrictive sense.

What is claimed is:

1. A field device for measuring one of a filling level, a pressure and a density of a medium in a container, comprising:

a data memory storing data of first and second program modules, the data memory including at least two memory areas: a first memory area and a second memory area, the first area being separated from the second area, wherein the data of the first and second program modules includes first data and second data, the first data being required for a safe operation of the field device and categorized as safety-critical, the second data not being required for the safe operation of the field device and categorized as safety-uncritical, wherein the first memory area stores the first data and the second memory area only stores the second data, wherein the first program modules are categorized as safety-critical and have access to the data stored in the first memory area, wherein the second program modules are categorized as safety-uncritical and do not have access to the data stored in the first memory area, wherein a measured value is stored in the first memory area as well as in the second memory area, wherein the first memory area includes a first data of a first program module that is designed for executing a function that is selected from the group comprising at least one of determination of measured values as a function of sensor measuring data, derivation of additional measured values as a function of already determined measured values, and output of measured values, which the first program module is configured to access the measured value stored in the first memory area, and wherein the second memory area includes a second data of a second program module that is designed for executing a function that is selected from the group comprising at least one of recording measured values with status information as a function of the time and indicating measured values, which the second program module is configured to access the measured value stored in the second memory area.

2. The field device of claim 1, further comprising:
a memory management unit,
wherein the separation of the first and second areas is realized in such a way that the memory management unit manages all access to the data.

3. The field device of claim 2, wherein a real-time operating system is provided that corresponds to safety requirements of the field device and supports the memory management unit.

4. The field device of claim 3, wherein the operating system allows communications between the program modules.

5. The field device of claim 1, wherein the field device cyclically processes the determination of measured values, the derivation of measured values and the output of measured values.

6. The field device of claim 5, further comprising:
a measured value recorder,
wherein the field device determining the diagnosis parallel to the acquisition of measured values, the measured value recorder checking after each determination of a measured value if the corresponding measured value needs to be recorded; and
wherein the measured value is stored in the first area and the second area.

7. The field device of claim 1, wherein the field device includes one of a filling level radar, an ultrasonic level measuring device and a limit level measuring device.

8. The field device of claim 1, wherein the first area stores the first data and first program modules that are required for the safe operation of the field device and categorized as a safety-critical; and wherein the second memory area only stores the second data and second program modules that are not required for the safe operation of the field device and categorized as safety-uncritical.

9. A method for measuring and determining one of a filling level, a pressure and a density of a medium in a container using a field device, comprising:
executing first program modules that are required for a safe operation of the field device and categorized as safety-critical, wherein first data relating to the first program modules is stored in a first memory area of a data memory;
executing second program modules that are not required for the safe operation of the field device and categorized as safety-uncritical, wherein second data relating to the second program modules is stored in a second memory area of the data memory;
storing a measured value redundantly in the first memory area as well as in the second memory area,
accessing the measured value stored in the first memory area with a first program module that is designed for executing a function that is selected from the group comprising at least one of determination of measured values as a function of sensor measuring data, derivation of additional measured values as a function of already determined measured values, and output of measured values, and
accessing the measured value stored in the second memory area with a second program module that is designed for executing a function that is selected from the group comprising at least one of recording measured values with status information as a function of the time and indicating measured values,
wherein the first area is separated from the second area, and
wherein program modules that are categorized as safety-uncritical do not have access to the data stored in the first memory area.

10. The method of claim 9, further comprising:
initiating a communication between the first and second areas using an operating system that corresponds to safety requirements of the field device.

11. A program element embodied on a non-transitory computer-readable medium for measuring and determining one of a filling level, a pressure and a density of a medium in a container using a field device, wherein the program element instructs a processor to carry out the following steps when it is executed on the processor:
executing first program modules that are required for a safe operation of the field device and categorized as safety-critical, wherein first data relating to the first program modules is stored in a first memory area of a data memory;
executing second program modules that are not required for the safe operation of the field device and categorized as safety-uncritical, wherein second data relating to the second program modules is stored in a second memory area of the data memory;
storing a measured value redundantly in the first memory area as well as in the second memory area,
accessing the measured value stored in the first memory area with a first program module that is designed for executing a function that is selected from the group comprising at least one of determination of measured values as a function of sensor measuring data, derivation of additional measured values as a function of already determined measured values, and output of measured values, and
accessing the measured value stored in the second memory area with a second program module that is designed for executing a function that is selected from the group comprising at least one of recording measured values with status information as a function of the time and indicating measured values,
wherein the first area is separated from the second area, and
wherein program modules that are categorized as safety-uncritical do not have access to the data stored in the first memory area.

12. A non-transitory machine-readable medium, on which a program element for measuring and determining one of a level, a pressure and a density of a medium in a container using a field device is stored, wherein the program element instructs a processor to carry out the following steps when it is executed on the processor:
executing first program modules that are required for a safe operation of the field device and categorized as safety-critical, wherein first data relating to the first program modules is stored in a first memory area of a data memory;
executing second program modules that are not required for the safe operation of the field device and categorized as safety-uncritical, wherein second data relating to the second program modules is stored in a second memory area of the data memory;

storing a measured value redundantly in the first memory area as well as in the second memory area, accessing the measured value stored in the first memory area with a first program module that is designed for executing a function that is selected from the group comprising at least one of determination of measured values as a function of sensor measuring data, derivation of additional measured values as a function of already determined measured values, and output of measured values, and accessing the measured value stored in the second memory area with a second program module that is designed for executing a function that is selected from the group comprising at least one of recording measured values with status information as a function of the time and indicating measured values, wherein the first area is separated from the second area, and wherein program modules that are categorized as safety-uncritical do not have access to the data stored in the first memory area.

* * * * *